United States Patent [19]
Clark et al.

[11] Patent Number: 6,011,023
[45] Date of Patent: *Jan. 4, 2000

[54] ANGIOSTATIC STEROIDS

[75] Inventors: Abbot F. Clark, Arlington; Raymond E. Conrow, Fort Worth, both of Tex.

[73] Assignee: Alcon Laboratories, Inc., Fort Worth, Tex.

[*] Notice: This patent is subject to a terminal disclaimer.

[21] Appl. No.: 08/924,419

[22] Filed: Aug. 27, 1997

Related U.S. Application Data

[63] Continuation of application No. 08/232,185, filed as application No. PCT/US92/10133, Nov. 23, 1992, abandoned.

[51] Int. Cl.[7] ............... A01N 45/00; C07J 53/00; C07J 5/00; C07J 7/00
[52] U.S. Cl. ............... 514/171; 552/501; 552/585; 552/592
[58] Field of Search .......... 514/171; 552/501, 552/585, 592

[56] References Cited

U.S. PATENT DOCUMENTS

| | | | |
|---|---|---|---|
| 4,771,042 | 9/1988 | Braughler et al. | 514/171 |
| 4,863,912 | 9/1989 | Southren et al. | 514/177 |
| 4,876,250 | 10/1989 | Clark | 514/179 |
| 4,945,089 | 7/1990 | Clark et al. | 514/171 |
| 4,975,537 | 12/1990 | Aristoff et al. | 540/9 |
| 4,997,826 | 3/1991 | Southren et al. | 514/177 |
| 5,371,078 | 12/1994 | Clark et al. | 514/182 |
| 5,407,926 | 4/1995 | Clark | 514/179 |
| 5,679,666 | 10/1997 | Clark | 514/179 |
| 5,719,167 | 2/1998 | Doshi et al. | 514/337 |

FOREIGN PATENT DOCUMENTS

| | | |
|---|---|---|
| WO 87/02672 | 5/1987 | WIPO. |
| WO 91/03245 | 3/1991 | WIPO. |

OTHER PUBLICATIONS

Crum, et al., A New Class of Steroids Inhibits Angiogenesis in the Presence of Heparin or a Heparin Fragment, Science, vol. 230, pp. 1375–1378 (Dec. 20, 1985).

Ingber, et al., A Possible Mechanism for Inhibition of Angiogenesis by Angiostatic Steroids: Induction of Capillary Basement Membrane Dissolution, Endocrinology vol. 119, pp. 1768–1775 (1986).

Li, et al., Angiostatic Steroids Potentiated by Sulphated Cyclodextrin Inhibit Corneal Neovascularization, Investigative Opthalmology and Visual Science, vol. 32, No. 11, pp. 2898–2905 (Oct., 1991).

Southren, et al., Intraocular Hypotensive Effect of a Topically Applied Cortisol Metabolite: 3–, 5–β tetrahydrocortisol, Investigative Ophthalmology and Visual Science, vol. 28, (May, 1987).

Folkman, et al., Angiostatic Steroids, Ann. Surg., vol. 206, No. 3 (1987).

Kitazawa, Increased Intraocular Pressure Induced by Corticosteroids, Am. J. Ophthal., vol. 82 pp. 492–493 (1976).

Cantrill, et al., Comparison of In Vitro Potency of Corticosteroids with Ability to Raise Intraocular Pressure, Am. J. Ophthal., vol. 79 pp. 1012–1016 (1975).

Mindel, et al., Comparative Ocular Pressure Elevation by Medrysone, Fluorometholone, and Dexamethasone Phosphate, Arch. Ophthal., vol. 98 pp. 1577–1578 (1980).

Furcht, Critical Factors Controlling Angiogenesis: Cell Products, Cell Matrix, and Growth Factors Laboratory Investigation, vol. 55, No. 5, pp. 505–509 (1986).

Cariou, et al., Inhibition of Human Endothelial Cell Proliferation by Heparin and Steroids, Cell Biology International Reports, vol. 12, No. 12, pp. 1037–1047 (Dec., 1988).

(List continued on next page.)

*Primary Examiner*—C. H. Kelly
*Attorney, Agent, or Firm*—Sally Yeager

[57] ABSTRACT

Methods and compositions for preventing and treating neovascularization with steroids is disclosed.

14 Claims, 1 Drawing Sheet

OTHER PUBLICATIONS

Tokida, et al., Production of Two Variant Laminin Forms by Endothelial Cells and Shift of Their Relative Levels by Angiostatic Steroids, The Journal of Biological Chemistry, vol. 264, No. 30, pp. 18123–18129 (Oct. 25, 1990).

Maragoudakis, et al., Antiangiogenic Action of Heparin Plus Cortisone is Associated with Decreased Collagenous Protein Synthesis in the Chick Chorioallantoic Membrane System, The Journal of Pharmacology and Experimental Therapeutics, vol. 251, No. 2, pp. 679–682 (1989).

Ashino–Fuse, et al., Medroxyprogesterone Acetate, An Anti––Cancer and Anti–Angiogenic Steroid, Inhibits the Plasminogen Activator in Bovine Endothelial Cells, Int. J. Cancer, 44, pp. 859–864 (1989).

BenEzra, Neovasculogenic Ability of Prostaglandins, Growth Factors, and Synthetic Chemoattractants, American Journal of Ophthalmology, vol. 86, No. 4, pp. 455–461, (Oct., 1978).

Rohen, Johanness W., Why is Intraocular Pressure Elevated in Chronic Simple Glaucoma?, Ophthalmology, vol. 90(7), pp. 758–764, (1983).

Knepper, et al., Glycosaminoglycans and Outflow Pathways of the Eye and Brain, Pediatric Neuroscience, vol. 12, pp. 240–251, (1985/86).

Folkman et al., Angiogenic Factors, Science, vol. 235, pp. 442–447 (1987).

Johnson, et al., Glaucoma: An Overview, Mayo Clin. Proc., vol. 61, pp. 59–67 (Jan. 1986).

FIG. 1

ANGIOSTATIC STEROIDS

This application is a continuation of application Ser. No. 08/232,185, filed Jul. 1, 1994 abandoned, which is a 371 case of PCT/US/92/10133, filed Nov. 23, 1992.

BACKGROUND OF THE INVENTION

1. Field of the Invention

This invention relates to angiostatic steroids for controlling ocular hypertension. The compounds are also useful in preventing and treating neovascularization. Specifically, the invention is directed to new angiostatic steroids, pharmaceutical compositions comprising the angiostatic steroids, and methods of treatment which comprise administering these compositions to treat ocular hypertension, including controlling ocular hypertension associated with primary open angle glaucoma, and to treat neovascularization. In addition, the compounds can be used in combination with glucocorticoids to treat ocular inflammation without the significant intraocular pressure rise commonly associated with the use of glucocorticoids.

2. Description of Related Art

Steroids functioning to inhibit angiogenesis in the presence of heparin or specific heparin fragments are disclosed in Crum, et al., *A New Class of Steroids Inhibits Angiogenesis in the Presence of Heparin or a Heparin Fragment*, Science, Vol.230, pp.1375–1378 (Dec. 20, 1985). The authors refer to such steroids as "angiostatic" steroids. Included within the new class of steroids found to be angiostatic are the dihydro and tetrahydro metabolites of cortisol and cortexolone. In a follow-up study directed to testing a hypotehsis as to the mechanism by which the steroids inhibit angiogenesis, it was shown that heparin/angiostatic steroid compositions cause dissolution of the basement membrane scaffolding to which anchorage dependent endothelia are attached resulting in capillary involution; see, Ingber, et al., *A Possible Mechanism for Inhibition of Angiogenesis by Angiostatic Steroids: Induction of Capillary Basement Membrane Dissolution*, Endocrinology Vol. 119, pp.1768–1775 1986).

A group of tetrahydro steroids useful in inhibiting-angiogenesis is disclosed in International Patent Application No. PCT/US86/02189, Aristoff, et al., (The Upjohn Company). The compounds are disclosed for use in treating head trauma, spinal trauma, septic or traumatic shock, stroke and hemorrhage shock. In addition, the patent application discusses the utility of these compounds in embryo implantations and in the treatment of cancer, arthritis and arteriosclerosis. Some of the steroids disclosed in Aristoff et al. are disclosed in U.S. Pat. No. 4,771,042 in combination with heparin or a heparin fragment for inhibiting angiogenesis in a warm blooded animal.

Compositions of hydrocortisone, "tetrahydrocortisol-S," and U-72,745G, each in combination with a beta cyclodextrin, have been shown to inhibit corneal neovascularization: Li, et al., *Angiostatic Steroids Potentiated by Sulphated Cyclodextrin Inhibit Corneal Neovascularization*, Investigative Ophthalmology and Visual Science, Vol. 32, No. 11, pp. 2898–2905 (October, 1991). The steroids alone reduce neovascularization somewhat but are not effective alone in effecting regression of neovascularization.

Tetrahydrocortisol (THF) has been disclosed for its use in lowering the intraocular pressure (IOP) of rabbits made hypertensive with dexamethasone alone, or with dexamethasone/5-beta-dihydrocortisol; see Southern, et al., *Intraocular Hypotensive Effect of a Topically Applied Cortisol Metabolite: 3-alpha, 5-beta-tetrahydrocortisol*, Investigative Ophthalmology and Visual Science, Vol.28 (May, 1987). The authors suggest THF may be useful as an antiglaucoma agent. In U.S. Pat. No. 4,863,912, issued to Southren et al. on Sep. 5, 1989, pharmaceutical compositions containing THF and a method for using these compositions to control intraocular pressure are disclosed. THF has been disclosed as an angiostatic steroid in Folkman, et al., *Angiostatic Steroids*, Ann. Surg. Vol.206, No.3 (1987) wherein it is suggested angiostatic steroids may have potential use for diseases dominanted by abnormal neovascularization, including diabetic retinopathy, neovascular glaucoma and retrolental fibroplasia.

Many compounds classified as glucocorticoids, such as dexamethasone and prednisolone, are very effective in the treatment of inflammed tissues; however, when these compounds are topically applied to the eye to treat ocular inflammation, certain patients experience elevated intraocular pressure. Patients who experience these elevations when treated with glucocorticoids are generally referred to as "steroid responders." These pressure elevations are of particular concern to patients who already suffer from elevated intraocular pressures, such as glaucoma patients. In addition, there is always a risk that the use of glucocorticoids in patients having normal intraocular pressures will cause pressure rises great enough to damage ocular tissues. Since glucocorticoid therapy is frequently long term (i.e., several days or more), there is potential for significant damage to ocular tissue as a result of prolonged elevations in intraocular pressure attributable to that therapy.

The following articles may be referenced for further background information concerning the well-recognized association between ophthalmic glucocorticoid therapy and elevations in intraocular pressure:

Kitazawa, *Increased Intraocular Pressure Induced by Corticosteroids*, Am. J. Ophthal., Vol.82 pp.492–493 (1976);

Cantrill, et al., *Comparison of In Vitro Potency of Corticosteroids with Ability to Raise Intraocular Pressure*, Am. J. Ophthal., Vol.79 pp.1012–1016 (1975); and Mindel, et al., *Comparative Ocular Pressure Elevation by Medrysone, Fluorometholone, and Dexamethasone Phosphate*, Arch. Ophthal., Vol.98 pp.1577–1578 (1980).

Commonly assigned U.S. application Ser. No. 07/399,351 U.S. Pat. No. 4,945,089 discloses the use of the angiostatic steroid tetrahydrocortexolone in combination with a glucocorticoid to treat ocular inflammation without the intraocular pressure elevating effect commonly associated with topical administration of glucocorticoids. In addition, commonly assigned International Application No. PCT/US90/04071 discloses the angiostatic steroids of Aristoff, et al. in combination with glucocorticoids to treat ocular inflammation without significant increase in intraocular pressure.

SUMMARY OF THE INVENTION

This invention is directed to angiostatic steroids and methods of using compositions of these steroids in inhibiting neovascularization. The compositions containing the steroids can be used for treatment of angiogenesis dependent diseases, for example: head trauma, spinal trauma, septic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, neovascular glaucoma, nonunion fractures, Osler-Weber Syndrome, psoriasis, pyogenic granuloma, retrolental fibroplasia, pterigium, scleroderma, trachoma, vascular adhesions, and solid tumor growth. In particular, the angiostatic steroids and compositions thereof are useful for controlling ocular neovascularization.

The invention also encompasses methods for controlling ocular hypertension and glaucoma through the systemic or local administration of the compositions disclosed herein.

The present invention also includes the use of the angiostatic steroids in combination with glucocorticoids for the treatment of ocular inflammation. The addition of at least one angiostatic steroid makes it possible to employ the potent antiinflammatory glucocorticoids without producing significant elevations in intraocular pressure.

DETAILED DESCRIPTION OF PREFERRED EMBODIMENTS

The development of blood vessels for the purpose of sustaining viable tissue is known as angiogenesis or neovascularization. Agents which inhibit neovascularization are known by a variety of terms such as angiostatic, angiolytic or angiotropic agents. For purposes of this specification, the term "angiostatic agent" means compounds which can be used to control, prevent, or inhibit angiogenesis.

The angiostatic agents of the present invention are steroids or steroid metabolites. For purposes herein, the term "angiostatic steroids" means steroids and steroid metabolites which inhibit angiogenesis.

There is currently no effective method for controlling the neovascularization in angiogenesis-dependent diseases. In particular, ocular neovascularization has not been successfully treated in the past. Neovascularization of tissues in the front of the eye (i.e. the cornea, iris, and the trabecular meshwork) and other conditions, including conditions in the back of the eye, for example, retinal, subretinal, macular, and optical nerve head neovascularization, can be prevented and treated by administration of the steroids of this invention. The angiostatic steroids of the present invention are useful in preventing and treating neovascularization, including providing for the regression of neovascularization.

The angiostatic steroids can also be used for the control of ocular hypertension. In particular, the agents can be used for the treatment of primary open angle glaucoma.

The angiostatic steroids of the present invention have the following formula:

Structure [A]

Structure [B]

wherein $R_1$ is H, $\beta$-$CH_3$ or $\beta$-$C_2H_5$;

$R_2$ is F, $C_9$-$C_{11}$ double bond, $C_9$-$C_{11}$ epoxy, H or Cl;

$R_3$ is H, $OR_{26}$, $OC(=O)R_{27}$, halogen, $C_9$-$C_{11}$ double bond, $C_9$-$C_{11}$ epoxy, =O, —OH, —O— alkyl($C_1$-$C_{12}$), —OC(=O)alkyl($C_1$-$C_{12}$), —OC(=O)ARYL, —OC(=O) N(R)$_2$ or —OC(=O)OR$_7$, wherein ARYL is furyl, thienyl, pyrrolyl, or pyridyl and each of said moieties is optionally substituted with one or two ($C_1$-$C_4$)alkyl groups, or ARYL is —(CH$_2$)$_f$-phenyl wherein f is 0 to 2 and the phenyl ring is optionally substituted with 1 to 3 groups selected from chlorine, fluorine, bromine, alkyl($C_1$-$C_3$), alkoxy($C_1$-$C_3$), thioalkoxy-($C_1$-$C_3$), $Cl_3C$—, $F_3C$—, —$NH_2$ and —NHCOCH$_3$ and R is hydrogen, alkyl ($C_1$-$C_4$), or phenyl and each R can be the same or different, and $R_7$ is ARYL as herein defined, or alkyl($C_1$-$C_{12}$);

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is 5 is $CH_2CH_2OR_{26}$, $CH_2CH_2OC(=O)R_{27}$, H, OH, $CH_3$, F, =$CH_2$, $CH_2C(=O)OR_{28}$, $OR_{26}$, $O(C=O)R_{27}$ or $O(C=O)CH_2(C=O)OR_{26}$ $R_{10}$ is —C≡CH, —CH=$CH_2$, halogen, CN, $N_3$, $OR_{26}$, $OC(=O)R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, $OC(=O)R_{27}$, $NH_2$, $NHR_{26}$, NHC(=O)R$_{27}$, N($R_{26}$)$_2$, NC(=O)R$_{27}$, $N_3$, H, —OH, =O, —O—P(=O)(OH)$_2$, or —O—C(=O)—(CH$_2$)$_t$COOH where t is an integer from 2 to 6;

$R_{14}$ is H or forms a double bond with $R_{12}$;

$R_{15}$ is H, =O or —OH;

and $R_{23}$ with $R_{10}$ forms a cyclic phosphate;

wherein $R_9$ and $R_{15}$ have the meaning defined above;

or wherein $R_{23}$ is —OH, O—C(=O)—$R_{11}$, —OP(O)—(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON(R$_{18}$)—, —N(R$_{18}$)CO—, —O—, —S—, —S(O)—, or —S(O$_2$)—; $R_{18}$ is hydrogen or alkyl ($C_1$-$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2COOH$ wherein $R_{19}$ is —S—, —S(O)—, —S(O)$_2$—, —SO$_2$N($R_{20}$)—, or N($R_{20}$)SO$_2$—; and $R_{20}$ is hydrogen or lower alkyl-($C_1$–$C_4$); with the proviso that the total number of carbon atoms in $R_{20}$ and $(CH_2)_r$ is not greater than 10; or (2) —CO—COOH; or (3) CON($R_{21}$)CH($R_{22}$)COOH wherein $R_{21}$ is H and $R_{22}$ is H, $CH_3$, —$CH_2COOH$, —$CH_2CH_2COOH$, —$CH_2OH$, —$CH_2SH$, —$CH_2CH_2SCH_3$, or —$CH_2Ph$—OH wherein Ph—OH is p-hydroxyphenyl;

or $R_{21}$ is $CH_3$ and $R_{22}$ is H;

or $R_{21}$ and $R_{22}$ taken together are —$CH_2CH_2CH_2$—;

or —N($R_{21}$)CH($R_{22}$)COOH taken together is —NHCH$_2$CONHCH$_2$COOH; and pharmaceutically acceptable salts thereof;

with the proviso that except for the compound wherein $R_1$ is β-$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is α-F, $R_9$ is β-$CH_3$, $R_{10}$ is α-OH, $R_{13}$ and $R_{15}$ are =O and $R_{23}$ is —OP(O)—(OH)$_2$, $R_{13}$ is =O only when $R_{23}$ with $R_{10}$ forms the above described cyclic phosphate.

$R_{24}$=C, $C_1$–$C_2$ double bond, O;

$R_{25}$=C($R_{15}$)$CH_2$—$R_{23}$, OH, $OR_{26}$, OC(=O)$R_{27}$, $R_{26}$, COOH, C(=O)$OR_{26}$, CHOHCH$_2$OH, CHOHCH$_2$$OR_{26}$, CHOHCH$_2$OC(=O)$R_{27}$, $CH_2CH_2OH$, $CH_2CH_2OR_{26}$, $CH_2CH_2OC$(=O)$R_{27}$, $CH_2CN$, $CH_2N_3$, $CH_2NH_2$, $CH_2NHR_{26}$, $CH_2N(R_{26})_2$, $CH_2OH$, $CH_2OR_{26}$, $CH_2O$(C=O)$R_{27}$, $CH_2O$(P=O) (OH)$_2$, $CH_2O$(P=O) (OR$_{26}$)$_2$, $CH_2SH$, $CH_2S$—$R_{26}$, $CH_2SC$(=O)$R_{27}$, $CH_2NC$(=O)$R_{27}$, C(=O)CHR$_{28}$OH, C(=O)CHR$_{28}$OR$_{26}$, C(=O)CHR$_2$OC(=O)$R_{27}$ or $R_{10}$ and $R_{25}$ taken together may be =C($R_{28}$)$_2$, that is, an optionally alkyl substituted methylene group;

wherein $R_{26}$=$C_1$–$C_6$ (alkyl, branched alkyl, cycloalkyl, haloalkyl, aralkyl, aryl); $R_{27}$=$R_{26}$+$OR_{26}$; $R_{28}$=H, C1–C6 (alkyl, branched alkyl, cycloalkyl).

Excepted from the compounds of Structure [A] are the compounds wherein $R_1$ is β-$CH_3$ or β-$C_2H_5$;

$R_2$ is H or Cl;

$R_3$ is H, —O, —OH, —O-alkyl($C_1$–$C_{12}$), —OC(=O) alkyl($C_1$–$C_{12}$), —OC(=O)ARYL, —OC(=O)N(R)$_2$ or α-OC(=O)$OR_7$, wherein ARYL is furyl, thienyl, pyrrolyl, or pyridyl and each of said moieties is optionally substituted with one or two ($C_1$–$C_4$)alkyl groups, or ARYL is —$(CH_2)_f$-phenyl wherein f is 0 to 2 and the phenyl ring is optionally substituted with 1 to 3 groups selected from chlorine, fluorine, bromine, alkyl($C_1$–$C_3$), alkoxy($C_1$–$C_3$), thioalkoxy-($C_1$–$C_3$), $C_{13}$C—, $F_3$C—, —$NH_2$ and —NHCOCH$_3$ and R is hydrogen, alkyl ($C_1$–$C_4$), or phenyl and each R can be the same or different, and $R_7$ is ARYL as herein defined, or alkyl ($C_1$–$C_{12}$); or wherein $R_2$ and $R_3$ taken together are oxygen (—O—) bridging positions C-9 and C-11; or wherein $R_2$ and $R_3$ taken together form a double bond between positions C-9 and C-11;

or $R_2$ is α-F and $R_3$ is β-OH;

or $R_2$ is α-Cl and $R_3$ is β-Cl;

and $R_4$ is H, $CH_3$, Cl or F;

$R_5$ is H, OH, F, Cl, Br, $CH_3$, phenyl, vinyl or allyl;

$R_6$ is H or $CH_3$;

$R_9$ is H, OH, $CH_3$, F or =$CH_2$;

$R_{10}$ is H, OH, $CH_3$ or $R_{10}$ forms a second bond between positions C-16 and C-17;

$R_{12}$ is —H or forms a double bond with $R_{14}$;

$R_{13}$ is H, —OH, =O, —O—P(O)(OH)$_2$, or —O—C(=O)—(CH$_2$)$_t$COOH where t is an integer from 2 to 6;

$R_{14}$ is H or forms a double bond with $R_{12}$;

$R_{15}$ is =O or —OH;

and $R_{23}$ with $R_{10}$ forms a cyclic phosphate;

wherein $R_9$ and $R_{15}$ have the meaning defined above;

or wherein $R_{23}$ is —OH, O—C(=O)—$R_{11}$, —OP(O)—(OH)$_2$, or —O—C(=O)—(CH$_2$)$_t$COOH wherein t is an integer from 2 to 6; and $R_{11}$ is —Y—$(C_2)_n$—X—$(C_2)_m$—SO$_3$H, —Y'—$(C_2)_p$—X'—$(C_2)_q$—NR$_{16}$R$_{17}$ or —Z(CH$_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S(O$_2$)—; $R_{18}$ is hydrogen or alkyl ($C_1$–$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2COOH$ wherein $R_{19}$ is —S—, —S(O)—, —S(O)$_2$—, —SO$_2$N($R_{20}$)—, or N($R_{20}$)SO$_2$—; and $R_{20}$ is hydrogen or lower alkyl-($C_1$–$C_4$); with the proviso that the total number of carbon atoms in $R_{20}$ and $(CH_2)_r$ is not greater than 10; or (2) —CO—COOH; or (3) CON($R_{21}$)CH($R_{22}$)COOH wherein $R_{21}$ is H and $R_{22}$ is H, $CH_3$, —$CH_2COOH$, —$CH_2CH_2COOH$, —$CH_2OH$, —$CH_2SH$, —$CH_2CH_2SCH_3$, or —$CH_2Ph$—OH wherein Ph—OH is p-hydroxyphenyl;

or $R_{21}$ is $CH_3$ and $R_{22}$ is H;

or $R_{21}$ and $R_{22}$ taken together are —$CH_2CH_2CH_2$—;

or —N($R_{21}$)CH($R_{22}$)COOH taken together is —NHCH$_2$CONHCH$_2$COOH; and pharmaceutically acceptable salts thereof;

with the proviso that except for the compound wherein $R_1$ is β-$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is α-F, $R_9$ is β-$CH_3$, $R_{10}$ is α-OH, $R_{13}$ and $R_{15}$ are =O and $R_{23}$ is —OP(O)—(OH)$_2$, $R_{13}$ is =O only when $R_{23}$ with $R_{10}$ forms the above described cyclic phosphate.

Unless specified otherwise, all substituent groups attached to the cyclopentanophenanthrene moiety of Structures [A] and [B] may be in either the alpha or beta position. Additionally, the above structures include all pharmaceutically acceptable salts of the angiostatic steroids.

Preferred angiostatic steroids for the treatment of ocular hypertension, neovascular diseases and ocular inflammation are:

21-METHYL-5β-PREGNAN-3α,11β,17α,
21-TETROL-20-ONE 21-METHYL ETHER

3β-AZIDO-5β-PREGNAN-
11β,17α,21-TRIOL-20-ONE-21-ACETATE

3β-ACETAMIDO-5β-
PREGNAN-11β,17α,21-TRIOL-
20-ONE-21-ACETATE

5β-PREGNAN-11β,17α,21-TRIOL-20-ONE 20-(4-FLUOROPHENYL)THIO-21-NOR-
5β-PREGNAN-3α,17α-DIOL

20-AZIDO-21-NOR-5β-PREGNAN-3α,
17α-DIOL 20-(CARBETHOXYMETHYL)THIO-21-NOR-5β-
PREGNAN-3α,17α-DIOL

20-ACETAMIDO-21-NOR-5β-PREGNAN-3α,
17α-DIOL-3-ACETATE 16-(2-HYDROXYETHYL)-17β-METHYL-
5β-ANDROSTAN-3α,17α-DIOL

20-CYANO-21-NOR-5β-PREGNAN-3α,17α-DIOL

17α-METHYL-5β-ANDROSTAN-3α,17β-DIOL

21-NOR-5β-PREGN-17(20)-EN-3α-OL

21-NOR-5β-PREGN-17(20)-EN-3α-OL-3-ACETATE

21-NOR-5β-PREGN-17(20)-EN-3α-OL-16-ACETIC ACID-3-ACETATE

21-NOR-5β-PREGNAN-3α,17α,20-TRIOL

21-NOR-5β-PREGNAN-17α,20-DIOL-3-ACETATE 4,9(11)-PREGNADIEN-17α,21-DIOL-3,20-DIONE-21-ACETATE 4,9(11)-PREGNADIEN-17α,21-DIOL-3,20-DIONE

11-EPICORTISOL

17α-HYDROXYPROGESTERONE

Most preferred compounds for preventing and treating neovascularization are:

4,9(11)-Pregnadien-17α,21-diol-3,20-dione-21-acetate
21-Nor-5β-pregn-17(20)-en-3α,16-diol-3-acetate-16-(O-methyl)malonate
4,9(11)-Pregnadien-17α,21-diol-3,20-dione
21-Nor-5β-pregnan-3α,17α,20-triol-3-acetate
21-Nor-5α-pregnan-3α,17α,20-triol-3-phosphate The angiostatic steroids of the present invention are useful in inhibiting neovascularization and can be used in treating the neovascularization associated with: head trauma, spinal trauma, systemic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, neovascular glaucoma, nonunion fractures, Osler-Weber Syndrome, psoriasis, pyogenic granuloma, retrolental fibroplasia, pterigium, scleroderma, trachoma, vascular adhesions, and solid tumor growth.

In particular, the angiostatic steroids are useful in preventing and treating any ocular neovascularization, including, but not limited to: retinal diseases (diabetic retinopathy, chronic glaucoma, retinal detachment, sickle cell retinopathy, senile macular degeneration due to subretinal neovascularization); rubeosis iritis; inflammatory diseases; chronic uveitis; neoplasms (retinoblastoma, pseudoglioma); Fuchs' heterochromic iridocyclitis; neovascular glaucoma; corneal neovascularization (inflammatory, transplantation, developmental hypoplasia of the iris); neovascularization resulting following a combined vitrectomy and lensectomy; vascular diseases (retinal ischemia, choroidal vascular insufficiency, choroidal thrombosis, carotid artery ischemia); pterigium; neovascularization of the optic nerve; and neovascularization due to penetration of the eye or contusive ocular injury.

The initiation of new blood vessel formation may arise quite differently in various tissues or as a result of different diseases. Many substances have been found to induce neovascularization, see, Folkman, et al., *Angiogenic Factors,* Science, Volume 235, pp. 442–447 (1987). However, it is believed, that once initiated, the process of neovascularization is similar in all tissues regardless of the associated disease, Furcht, *Critical Factors Controlling Angiogenesis: Cell Products, Cell Matrix, and Growth Factors,* Laboratory Investigation, Volume 55, No. 5, pp. 505–509 (1986).

There are a variety of theories regarding the mechanism of action of angiostatic steroids. For example, angiostatic steroid induced inhibition of neovascularization may occur due to, dissolution of the capillary basement membrane, Ingber, et al., Supra; inhibition of vascular endothelial cell proliferation, Cariou, et al., *Inhibition of Human Endothelial Cell Proliferation by Heparin and Steroids,* Cell Biology International Reports, Vol. 12, No. 12, pp. 1037–1047 (December, 1988); effect on vascular endothelial cell laminin expression, Tokida, et al., *Production of Two Variant Laminin Forms by Endothelial Cells and Shift of Their Relative Levels by Angiostatic Steroids,* The Journal of Biological Chemistry, Vol. 264, No. 30, pp. 18123–18129 (Oct. 25, 1990); inhibition of vascular cell collagen synthesis, Maragoudakis, et al., *Antiangiogenic Action of Heparin Plus Cortisone is Associated with Decreased Collagenous Protein Synthesis in the Chick Chorioallantoic Membrane System,* The Journal of Pharmacology and Experimental Therapeutics, Vol. 251, No. 2, pp. 679–682 (1989); and inhibition of vascular endothelial cell plasminogen activator activity, Ashino-Fuse, et al., *Medroxyprogesterone Acetate, An Anti-Cancer and Anti-Angiogenic Steroid, Inhibits the Plasminogen Activator in Bovine Endothelial Cells,* Int. J. Cancer, 44, pp. 859–864 (1989).

There are many theories associated with the cause of neovascularization, and there may be different inducers depending on the disease or surgery involved, BenEzra, *Neovasculogenic Ability of Prostaglandins, Growth Factors, and Synthetic Chemoattractants,* American Journal of Ophthalmology, Volume 86, No. 4, pp. 455–461, (October, 1978). Regardless of the cause or the associated disease or surgery, it is believed that angiostatic agents work by inhibiting one or more steps in the process of neovascularization. Therefore, the angiostatic steroids of this invention are useful in the treatment and prevention of neovascularization associated with a variety of diseases and surgical complications.

The angiostatic steroids of the present invention may be incorporated in various formulations for delivery. The type of formulation (topical or systemic) will depend on the site of disease and its severity. For administration to the eye, topical formulations can be used and can include ophthalmologically acceptable preservatives, surfactants, viscosity enhancers, buffers, sodium chloride, and water to form aqueous sterile ophthalmic solutions and suspensions. In order to prepare sterile ophthalmic ointment formulations, an angiostatic steroid is combined with a preservative in an appropriate vehicle, such as mineral oil, liquid lanolin, or white petrolatum. Sterile ophthalmic gel formulations comprising the angiostatic steroids of the present invention can be prepared by suspending an angiostatic steroid in a hydrophilic base prepared from a combination of, for example, Carbopol® (a carboxy vinyl polymer available from the BF Goodrich Company) according to published formulations for analogous ophthalmic preparations. Preservatives and antimicrobial agents may also be incorporated in such gel formulations. Systemic formulations for treating ocular neovascularization can also be used, for example, orally ingested tablets and formulations for intraocular and periocular injection.

The specific type of formulation selected will depend on various factors, such as the angiostatic steroid or its salt being used, the dosage frequency, and the location of the neovascularization being treated. Topical ophthalmic aqueous solutions, suspensions, ointments, and gels are the preferred dosage forms for the treatment of neovascularization in the front of the eye (the cornea, iris, trabecular meshwork); or neovascularization of the back of the eye if the angiostatic agent can be formulated such that it can be delivered topically and the agent is able to penetrate the tissues in the front of the eye. The angiostatic steroid will normally be contained in these formulations in an amount from about 0.01 to about 10.0 weight/percent. Preferable concentrations range from about 0.1 to about 5.0 weight/percent. Thus, for topical administration, these formulations are delivered to the surface of the eye one to six times a day, depending on the routine discretion of the skilled clinician. Systemic administration, for example, in the form of tablets is useful for the treatment of neovascularization particularly of the back of the eye, for example, the retina. Tablets containing 10–1000 mg of angiostatic agent can be taken 2–3 times per day depending on the discretion of the skilled clinician.

The preferred compounds for controlling ocular hypertension are: 21-Nor-5β-pregnan-3α,17α,20-triol; 5β-pregnan-11β,17α,21-triol-20-one; 4,9(11)-Pregnadien-17α,21-diol-3,20-dione-21-acetate, and 4,9(11)-Pregnadien-17α,21-diol-3,20-dione. The most preferred compound is 4,9(11)-Pregnadien-17α,21-diol-3,20-dione-21-acetate.

Without intending to be bound by any theory, it is believed that the angiostatic steroids of the type described above act to control intraocular pressure by inhibiting the accumulation or stimulating the dissolution of amorphous extracellular material in the trabecular meshwork of the eye. The presence of this amorphous extracellular material alters the integrity of the healthy trabecular meshwork and is a symptom associated with primary open angle glaucoma (POAG). It is not well understood why this amorphous extracellular material builds up in the trabecular meshwork of persons suffering from POAG. However, it has been found that the amorphous extracellular material is generally composed of glycosaminoglycans (GAGs) and basement membrane material; see, *Ophthalmology,* Vol.90, No.7 (July 1983); *Mayo Clin. Proc,* Vol.61, pp.59–67 (January 1986); and *Pediat. Neurosci.* Vol.12, pp.240–251 (1985–86). When these materials build up in the trabecular meshwork, the aqueous humor, normally present in the anterior chamber of the eye, cannot leave this chamber through its normal route (the trabecular meshwork) at its normal rate. Therefore, a normal volume of aqueous humor is produced by the ciliary processes of the eye and introduced into the anterior chamber, but its exit through the trabecular meshwork is abnormally slow. This results in a buildup of pressure in the eye, ocular hypertension, which can translate into pressure on the optic nerve. The ocular hypertension so generated can lead to blindness due to damage to the optic nerve.

Many methods for treating primary open angle glaucoma and ocular hypertension concentrate on blocking production of aqueous humor by the eye. However, aqueous humor is the fundamental source of nourishment for the tissues of the eye, particularly the cornea and lens which are not sustained by blood supply. Therefore, it is not desirable to deprive these tissues of the necessary irrigation and nutrition provided by the aqueous humor. It is desirable to strive for normal exit of the aqueous humor by maintaining the normal integrity of the trabecular meshwork. This is accomplished according to the present invention by the administration of angiostatic steroids.

It is believed that the angiostatic steroids disclosed herein function in the trabecular meshwork in a similar manner as shown by Ingber, et al., wherein it was shown that angiostatic steroids caused dissolution of the basement membrane scaffolding using a chick embryo neovascularization model; *Endocrinology*, 119, pp.1768–1775 (1986). It is believed that the angiostatic steroids of the present invention prevent the accumulation, or promote the dissolution of, amorphous extracellular materials in the trabecular meshwork by inhibiting the formation of basement membrane materials and glycosaminoglycans. Thus, by preventing the development of these materials or promoting their dissolution, the normal integrity of the trabecular meshwork is retained and aqueous humor may flow through the trabecular meshwork at normal rates. As a result, the intraocular pressure of the eye is controlled.

The angiostatic steroids of the present invention may be incorporated in various formulations for delivery to the eye to control ocular hypertension. For example, topical formulations can be used and can include ophthalmologically acceptable preservatives, surfactants, viscosity enhancers, buffers, sodium chloride and water to form aqueous sterile ophthalmic solutions and suspensions. In order to prepare sterile ophthalmic ointment formulations, an angiostatic steroid is combined with a preservative in an appropriate vehicle, such as mineral oil, liquid lanolin or white petrolatum. Sterile ophthalmic gel formulations comprising the angiostatic steroids of the present invention can be prepared by suspending an angiostatic steroid in a hydrophilic base prepared from a combination of, for example, Carbopol® 940 (a carboxyvinyl polymer available from the B.F. Goodrich Company) according to published formulations for analogous ophthalmic preparations. Preservatives and tonicity agents may also be incorporated in such gel formulations. The specific type of formulations selected will depend on various factors, such as the angiostatic steroid or its salt being used, and the dosage frequency. Topical ophthalmic aqueous solutions, suspensions, ointments and gels are the preferred dosage forms. The angiostatic steroid will normally be contained in these formulations in an amount of from about 0.005 to about 5.0 weight percent (wt. %). Preferable concentrations range from about 0.05 to about 2.0 wt. %. Thus, for topical administration, these formulations are delivered to the surface of the eye one to four times per day, depending upon the routine discretion of the skilled clinician.

In addition, antiinflammatory compositions of glucocorticoids can contain one or more angiostatic steroids of the present invention, preferably tetrahydrocortisol. These compositions will contain one or more glucocorticoids in an antiinflammatory effective amount and will contain one or more angiostatic steroids of the present invention in an amount effective to inhibit the IOP elevating effect of the glucocorticoids. The amount of each component will depend on various factors, such as the relative tendency of certain glucocorticoids to cause IOP elevations, the severity and type of ocular inflammation being treated, the estimated duration of the treatment, and so on. In general, the ratio of the amount of glucocorticoid to the amount of angiostatic steroid on a weight to weight basis will be in the range of 10:1 to 1:20. The concentration of the glucocorticoid component will typically be in the range of about 0.01% to about 2.0% by weight. The concentration of the angiostatic steroid component will typically be in the range of about 0.05% to about 5.0% by weight.

The above-described active ingredients may be incorporated into various types of systemic and ophthalmic formulations. For example, for topical ocular administration, the active ingredients may be combined with ophthalmologically acceptable preservatives, surfactants, viscosity enhancers, buffers, toxicity agents and water to form an aqueous, sterile ophthalmic suspension. In order to prepare sterile ophthalmic ointment formulations, the active ingredients are combined with a preservative in an appropriate vehicle, such as mineral oil, liquid lanolin, or white petrolatum. Sterile ophthalmic gel formulations may be prepared by suspending the active ingredient in a hydrophilic base prepared from the combination of Carbopol® 940 (a carboxy vinyl polymer available from the B.F. Goodrich Company) according to published formulations for analogous ophthalmic preparations; preservatives and tonicity agents can also be incorporated. The specific type of formulation selected will depend on various factors, such as the severity and type of ophthalmic inflammation being treated, and dosage frequency. Ophthalmic solutions, suspensions, ointments and gels are the preferred dosage forms, and topical application to the inflamed ocular tissue is the preferred route of administration.

The following examples illustrate formulations and synthesis of compounds of the present invention, but are in no way limiting.

EXAMPLE 1

The topical compositions are useful for controlling ocular hypertension or controlling ocular neovascularization.

| Component | wt. % |
| --- | --- |
| Angiostatic Steroid | 0.005–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 2

The composition is useful for controlling ocular hypertension.

| Component | wt. % |
| --- | --- |
| 21-Nor-5β-pregnan-3α,17α,20-triol | 1.0 |
| Tyloxapol | 0.01–0.05 |
| HPMC | 0.5 |
| Benzalkonium Chloride | 0.01 |

-continued

| Component | wt. % |
|---|---|
| Sodium Chloride | 0.8 |
| Edetate Disodium | 0.01 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1 M NaOH/HCl. The solution is then sterilized by means of filtration.

21-Nor-5β-pregnan-3α,17α,20-triol is sterilized by either dry heat or ethylene oxide. If ethylene oxide sterilization is selected, aeration for at least 72 hours at 50° C. is necessary. The sterilized steroid is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 3

The following formulation is representative of the antiinflammatory compositions of the present invention.

| Component | wt. % |
|---|---|
| 4,9(11)Pregnadien-17α,21-diol-3,20-dione-21-acetate | 1.0 |
| Dexamethasone | 0.1 |
| Tyloxapol | 0.01 to 0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

The above formulation is prepared in the same manner set forth in Example 2, sterilizing and adding the dexamethasone to the steroid before placing both into a pressurized ballmill container.

EXAMPLE 4

The following formulation is another example of the antiinflammatory compositions of the present invention.

| | wt. % |
|---|---|
| Tetrahydrocortisol | 1.0 |
| Prednisolone Acetate | 1.0 |
| Tyloxapol | 0.01 to 0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mls |

The above formulation is prepared in the same manner set forth in Example 2, sterilizing and adding the prednisolone acetate to the steroid before placing both into a pressurized ballmill container.

The following formulations are representative of compositions used for the treatment of angiogenesis dependent diseases.

EXAMPLE 5

Formulation For Topical Oral Administration

Tablet:

10–1000 mg of angiostatic steroid with inactive ingredients such as starch, lactose and magnesium stearate can be formulated according to procedures known to those skilled in the art of tablet formulation.

EXAMPLE 6

| FORMULATION FOR STERILE INTRAOCULAR INJECTION | |
|---|---|
| each mL contains: | |
| Angiostatic Steroid | 10–100 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloric acid or sodium hydroxide to adjust pH to approximately 7.2 | |
| Water for injection | |

EXAMPLE 7

| FORMULATION FOR TOPICAL OCULAR SOLUTION | |
|---|---|
| 21-Nor-5α-pregnan-3α,17α-20-triol-3-phosphate | 1.0% |
| Benzalkonium chloride | 0.01% |
| HPMC | 0.5% |
| Sodium chloride | 0.8% |
| Sodium phosphate | 0.28% |
| Edetate disodium | 0.01% |
| NaOH/HCl | q.s. pH 7.2 |
| Purified Water | q.s. 100 mL |

EXAMPLE 8

| FORMULATION FOR TOPICAL OCULAR SUSPENSION | |
|---|---|
| Ingredient | Amount (wt. %) |
| 4,9(11)-Pregnadien-17α,21-diol-3,20-dione-21-acetate | 1.0 |
| Tyloxapol | 0.01 to 0.05 |
| HPMC | 0.5 |
| Benzalkonium chloride | 0.01 |
| Sodium chloride | 0.8 |
| Edetate Disodium | 0.01 |
| NaOH/HCl | q.s. pH 7.4 |
| Purified Water | q.s. 100 mL |

The formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1 M NaOH/HCl. The solution is then sterilized by means of filtration.

The 4,9(11)-Pregnadien-17a,21-diol-3,20-dione-21-acetate is sterilized by either dry heat or ethylene oxide. If ethylene oxide sterilization is selected, aeration for at least 72 hours at 50° C. is necessary. The sterilized 4,9(11)-Pregnadien-17a,21-diol-3,20-dione-21-acetate is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl. The formulation will be given topically, in a therapeutically effective amount. In this instance, the phrase "therapeutically effective amount" means an amount which is sufficient to substantially prevent or reverse any ocular neovascularization. The dosage regimen used will depend on the nature of the neovascularization, as well as various other factors such as the patient's age, sex, weight, and medical history.

EXAMPLE 9

Formulation For Oral Administration

Tablet:

5–100 mg 21-Nor-5β-pregnan-3α-17α-20-triol with inactive ingredients such as starch, lactose and magnesium stearate can be formulated according to procedures known to those skilled in the art of tablet formulation.

EXAMPLE 10

| Formulation for Sterile Intraocular Injection | |
|---|---|
| each mL contains: | |
| 4,9(11)-Pregnadien-17α,21-diol-.3,20-dione | 10–100 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloric acid or sodium hydroxide to adjust pH to approximately 7.2 | |
| Water for injection | |

EXAMPLE 11

Figure 1:
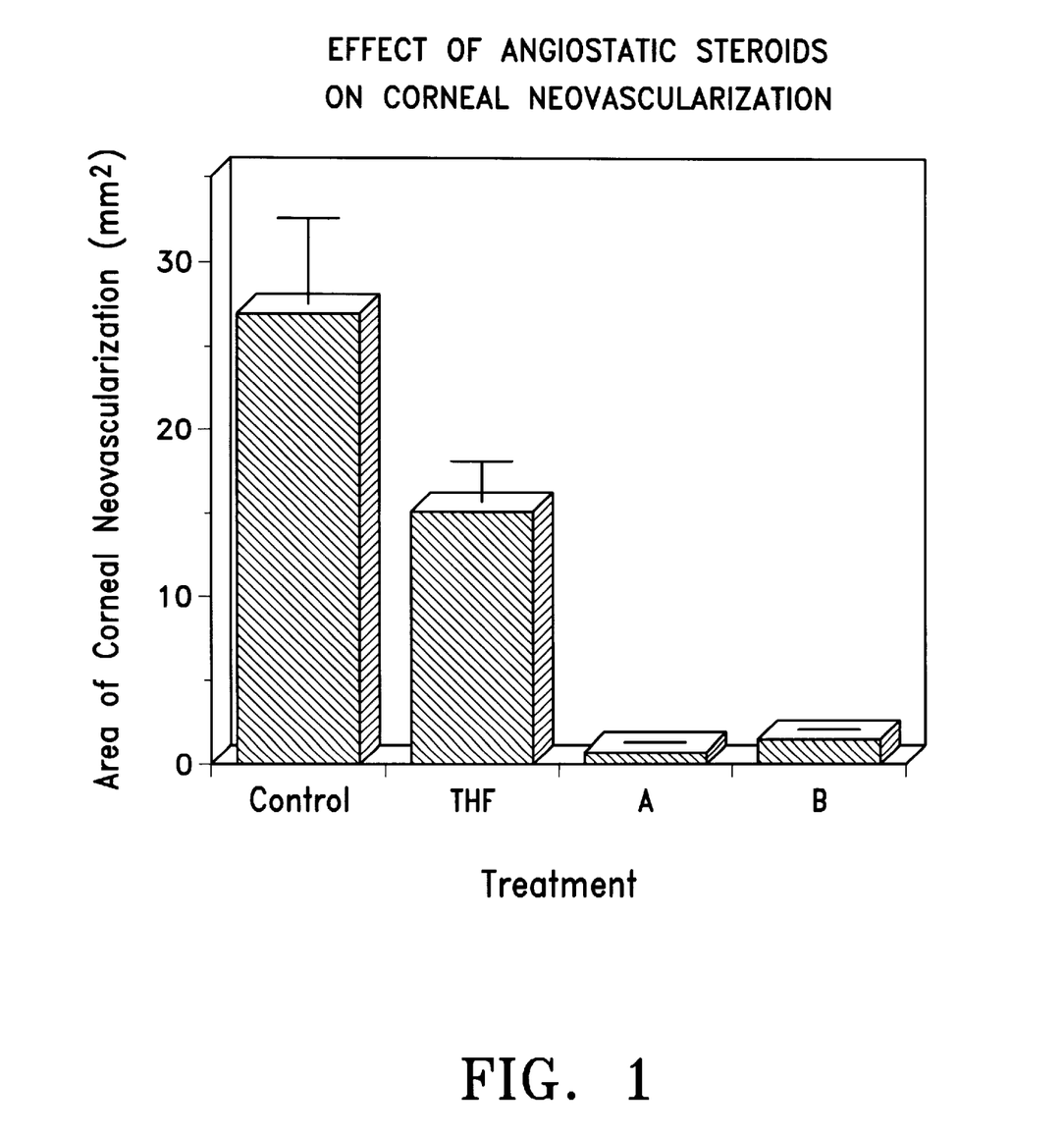
FIG. 1 compares the ability of angiostatic steroids to inhibit neovascularization in the rabbit cornea.

Inhibition of angiogenesis in the rabbit corneal neovascularization model:

The corneal pocket system of BenEzra (Am. J. Ophthalmol 86:455–461, 1978) was used to induce corneal neovascularization in the rabbit. A small Elvax pellet containing 0.5 μg of lipopolysaccharide (LPS) was inserted into the middle of the corneal stroma and positioned 2.5 mm from the limbus. An additional Elvax pellet with or without 50 μg of angiostatic steroid was placed next to the LPS implant. The eyes were examined daily and the area of neovascularization calculated. Results after 8 days of LPS implantation are shown in FIG. 1. THF—tetrahydrocortisol; A=4,9(11)-Pregnadien-17α,21-diol-3,20-dione-21-acetate; B=4,9(11)-Pregnadien-17α,21-diol-3,20-dione. As can be seen, A & B totally inhibited corneal neovascularization, whereas THF partially inhibited the neovascular response.

EXAMPLE 12

Preparation of 5β-Pregnan-11β,17α,21-triol-20-one Tetrahydrocortisol-F-21-t-butyldiphenylsilyl ether (PS03842)

A solution of 4.75 g (17.3 mol) of t-butyldiphenylchlorosilane in 5 mL of dry DMF was added dropwise to a stirred solution of 5.7 g (15.6 mmol) of tetrahydrocortisol-F (Steraloids No. P9050) and 2.3 g (19 mmol) of 4-dimethylaminopyridine (DMAP) in 30 mL of dry DMF, under $N_2$, at −25 to −30° C. (maintained with $CO_2$—MeCN). After a further 20 min at −30° C., the mixture was allowed to warm to 23° C. overnight.

The mixture was partitioned between ether and water, and the organic solution was washed with brine, dried ($MgSO_4$), filtered and concentrated to give 10.7 g of a white foam.

This material was purified by flash column chromatography (400 g silica; 62.5 to 70% ether/hexane). The 3-siloxy isomer eluted first, followed by mixed fractions, followed by the title compound. The concentrated mixed fractions (4.0 g) were chromatographed on the same column with 35% ethyl acetate/hexane. The total yield of the 3-siloxy isomer was 0.42 g (5%), and of the title compound, 5.05 g (53.5%). Continued elution with 25% NeOH/EtOAc allowed recovery of unreacted tetrahydrocortisol-F.

PS03842

NMR (200 MHz $^1$H) ($CDCl_3$): δ0.63 (s, 3H, Me-18); 1.11 (s, 9H, t-Bu); 1.12 (s, 3H, Me-19); 2.57 (t, J-13, 1H, H-8); 2.6 (s, 1H, OH-17); 3.63 (sept, J=2.5, 1H, H-3); 4.15 (br s, 1H, H-11); 4.37 and 4.75 (AB, J-20, 2H, H-21); 7.4 (m, 6H) and 7.7 (m, 4H) ($Ph_2$).

NMR (200 MHz $^1$H) (DMSO-d$_6$): δ0.64 (s, 3H, Me-18); 1.02 (s, 9H, t-Bu); 1.07 (s, 3H, Me-19); 2.50 (t, J=13, 1H, H-8); 3.37 (m, 1H, H-3); 3.94 (d, J=2, 1H, OH-11); 4.00 (br s, 1H, H-11); 4.42 (d, J=5, 1H, OH-3); 4.38 and 4.83 (AB, J=20, 2H, H-21); 5.11 (s, 1H, OH-17); 7.45 (m, 6H) and 7.6 (m, 4H) (Ph$_2$).

NMR (50.3-MHz $^{13}$C) (CDCl$_3$): 17.4 (C-18); 19.3 (C-16); 23.7 (C-15); 26.3 (C-7); 26.6 (C-19); 26.8 (Me$_3$C); 27.2 (C-6); 30.9 (C-2); 31.5 (C-8); 34.1 (Me$_3$C); 34.8 (C-10); 35.2 (C-1); 36.2 (C-4); 39.7 (C-13); 43.5 (C-5); 44.3 (C-9); 47.4 (C-12); 52.1 (C-14); 67.8 (C-11); 68.9 (C-21); 71.7 (C-3); 89.8 (C-14); 127.8, 129.8, 132.8, 132.9, 135.7, 135.8 (diastereotopic Ph$_2$); 208.8 (C-20). Underlined resonances showed inversion in the APT experiment. Assignments: E. Breitmaier, W. Voelter "Carbon-13 NMR Spectroscopy," 3d ed., VCH, 1987; pp. 345–348.

IR (KBr) 3460, 2930, 2860, 1720, 1428, 1136, 1113, 1070, 1039, 703 cm$^{-1}$.

This compound did not show a sharp melting point but turned to a foam at 80–100° C. Numerous attempts at recrystallization failed.

5β-Pregnan-11β,17α,21-triol-20-one

A solution of PS03842 (0.91 g, 1.50 mmol) and thiocarbonyl diimidazole (1.05 g, 5.9 mol) in 8 mL of anhydrous dioxane was refluxed under N$_2$ for 3.5 h. The cooled solution was partitioned between ether and water and the organic solution was washed with brine, dried (MgSO$_4$), filtered and concentrated. The residue was chromatographed (120 g SiO$_2$, 35% EtOAc/hexane) giving 0.86 g (80%) of the imidazolyl thioester.

A solution of 0.75 g (1.05 mmol) of this compound in 100 mL of anhydrous dioxane was added dropwise over 2.2 h to a rapidly stirred, refluxing solution of 1.6 mL (5.9 mmol) of Bu$_3$SnH in 100 mL of anhydrous dioxane under N$_2$. After a further 1 h at reflux, the solution was cooled, concentrated and the residue chromatographed (200 g SiO$_2$, 9% EtOAc/hexane) giving 0.43 g (70%) of the 3-deoxy-21-silyl ether. This material was dissolved in 20 mL of methanol; Bu$_4$NF.3H$_2$O (0.50 g, 1.6 mmol) was added, and the mixture was heated to reflux under N$_2$ for 4 h. The cooled solution was diluted with 2 volumes of EtOAc, concentrated to ¼ volume, partitioned (EtOAc/H$_2$O), and the organic solution was washed with brine, dried (MgSO$_4$), filtered and concentrated. The residue (0.40 g) was chromatographed (30 g SiO$_2$, 40% EtOAc/hexane) to give 0.25 g (98%) of an oil.

This oil was crystallized (n-BuCl) to afford 0.14 g of the title compound as a white solid, m.p. 167–170° C.

IR (KBr): 3413 (br), 2934, 1714, 1455, 1389, 1095, 1035 cm$^{-1}$.

MS (CI): 351 (M+1).

NMR (200 MHz $^1$H, DMSO-d$_6$): δ0.69 (s, 3H, Me-18); 1.14 (s, 3H, Me-19); 0.8–2.0 (m); 2.5 (t, J=13, 1H, H-8); 3.96 (d, J-2, 1H, OH-11); 4.1 (br s, 1H, H-11); 4.1 and 4.5 (AB, further split by 5 Hz, 2H, H-21); 4.6 (t, J=5, 1H, OH-21); 5.14 (s, 1H, OH-17). Anal. Calc'd for C$_{21}$H$_{34}$O$_4$: C, 71.96; H, 9.78. Found: C, 71.69; H, 9.66.

EXAMPLE 13

Preparation of 21-Methyl-5β-pregnan-3α,11β, 17α, 21-tetrol-20-one 21-methyl ether Sodium hydride (60% oil dispersion, 0.10 g, 2.5 mmol) was added to a stirred solution of tetrahydrocortisol-F (0.73 g, 2.0 mmol) and CH$_3$I (0.60 mL, 9.6 mmol) in 8 mL of anhydrous DMF under N$_2$. Hydrogen was evolved, and the temperature rose to 35° C. After 1 h, the mixture was diluted with EtOAc, extracted with water (until neutral) and brine, dried (MgSO$_4$), filtered and concentrated. The residue was chromatographed (70 g SiO$_2$, 80% EtOAc/hexane) to give 0.17 g of a white solid, MS (CI)=395 (M+1). This material was recrystallized (EtOAc-n-BuCl) to afford 0.12 g (16%) of the title compound as a feathery white solid, m.p. 208–213° C.

IR (KBr): 3530, 3452, 2939, 2868, 1696 (s, CO), 1456, 1366, 1049 cm$^{-1}$. NMR (200 MHz $^1$H, DMSO-d$_6$): δ0.74 (s, 3H, Me-18); 1.09 (s, 3H, Me-19); 1.14 (d, J=6.6, 3H, C-21 Me); 0.8–2.0 (m); 2.47 (t, J-13, 1H, H-8); 3.18 (s, 3H, OMe); 3.35 (m, 1H, H-3); 4.00 (d, J=2, 1H, OH-11); 4.07 (br s, 1H, H-11); 4.37 (q, J=6.6, 1H, H-21); 4.43 (d, J=5, 1H, OH-3); 5.16 (s, 1H, OH-17). Anal. Calc'd for C$_{23}$H$_{38}$O$_5$: C, 70.01; H, 9.71. Found: C, 70.06; H, 9.76.

EXAMPLE 14

Preparation of 3β-Azido-5β-pregnan-11β,17α,21-triol-20-one-21-acetate

A solution of triphenylphosphine (2.6 g, 10 mmol) in 10 mL of toluene was carefully added to a stirred solution of PS03842 (see Example 4) (1.75 g, 2.90 mmol), diphenylphosphoryl azide (2.2 mL, 10.2 mmol) and diethyl azodicarboxylate (1.55 mL, 10 mol) under N$_2$, keeping the internal temperature below 35° C. (exothermic). The solution was stirred for 1.2 h, then diluted with ether, washed with water and brine, dried (MgSO$_4$), filtered and concentrated and the residue (9.5 g, oil) chromatographed 175 g SiO$_2$, 15% EtOAc/hexane) giving 1.83 g of a viscous oil.

A solution of 1.73 g of this material and 1.75 g (5.5 mmol) of Bu$_4$NF.3H$_2$O in 20 mL of methanol was refluxed under N$_2$ for 2.5 h. The crude product (1.94 g) was isolated with ethyl acetate and chromatographed (100 g SiO$_2$, 50% EtOAc/hexane) giving 0.60 g (56%) of a white semisolid. Trituration (4:1 hexane-ether) gave 0.57 g (53%) of a solid.

A stirred solution of 0.40 g of this material in 3 mL of dry pyridine was treated with 0.3 mL of acetic anhydride and stirred overnight at 23° C. under N$_2$. The mixture was quenched with 1 mL of methanol, stirred for 15 min, diluted with ether, washed with 1 M aqueous HCl, water (until neutral), brine, dried (MgSO4), filtered and concentrated. The residue (0.41 g, oil) was chromatographed (35 g SiO$_2$, 33% EtOAc/hexane) to afford 0.33 g (76%) of the title compound as a white foam, m.p. 80–90° C. (dec).

IR (KBr): 3505, 2927, 2866, 2103 (vs), 1721 (sh 1730), 1268, 1235 cm$^{-1}$. NMR (200 MHz $^1$H, CDCl$_3$): δ0.92 (s, 3H, Me-18); 1.21 (s, 3H, Me-19); 1.0–2.1 (m); 2.17 (s, 3H, Ac); 2.25 (s 1H, OH-17); 2.74 (m, 1H, H-8); 3.97 (br s, 1H, H-3); 4.31 (br s, 1H, H-11); 4.94 (AB, J=17, Δv=60, 2H, H-21). Anal. Calc'd for C$_{23}$H$_{35}$N$_3$O$_5$: C, 63.72; H, 8.14; N, 9.69. Found: C, 63.39; H, 8.18; N, 9.45.

EXAMPLE 15

Preparation of 3β-Acetamido-5β-pregnan-11β,17α-21-triol-20-one-21-acetate

A solution of 3β-azido-5β-pregnan-11β,17α,21-triol-20-one-21-acetate (0.15 g, 0.35 mmol) in 8 mL of absolute ethanol containing 0.03 g of 10% Pd on C was stirred under H$_2$ ( 1 atm) at 23° C. for 2 h. The mixture was filtered and concentrated, the residue dissolved in EtOAc, the basic material extracted into 1 M aqueous HCl, liberated (Na$_2$CO$_3$), extracted (EtOAc) and the organic extract washed with water (until neutral) and brine, dried (MgSO$_4$), filtered and concentrated to provide 58 mg of a solid.

This material was acetylated (1.0 mL of dry pyridine, 0.20 mL of Ac$_2$O, 23° C., N$_2$, overnight), followed by workup (as described for the steroid of Example 14 [last step]) affording a crude product that was chromatographed (25 g $SiO_2$, EtOAc). This product was triturated with ether to afford 51 mg (33%) of product as a white solid, m.p. 179–181° C.

MS (CI, isobutane): (M+1)=450 ($M^+$), 432, 391, 371, 348.

IR (KBr): 3398 (br), 2932, 2865, 1720 (sh. 1740), 1652, 1538, 1375, 1265, 1236 $cm^{-1}$. NMR (200 MHz $^1H$, $CDCl_3$): δ0.89, 1.22, 1.99, 2.17 (all s, 3H); 1.0–2.2 (m); 2.7 (t, J=13, 1H, H-8); 3.03 (s, 1H, OH-17); 4.2 (br s, 1H, H-11); 4.3 (br s, 1H, H-3); 4.96 (AB, J=17.5, Δv32 42, 2H, H-21); 5.8 (d, J=10, 1H, NH).

We claim:

1. A method for preventing and treating neovascularization, which comprises: administering a therapeutically effective amount of a composition comprising a compound of the formula:

Structure [A]

Structure [B]

wherein $R_1$ is H, β-$CH_3$ or β-$C_2H_5$;

$R_2$ is F, $C_9$–$C_{11}$ double bond, $C_9$–$C_{11}$ epoxy, H or Cl;

$R_3$ is H, $OR_{26}$, OC(=O)$R_{27}$, halogen, $C_9$–$C_{11}$ double bond, $C_9$–$C_{11}$ epoxy, =O, —OH, —O— alkyl ($C_1$–$C_{12}$), —OC(=O)alkyl($C_1$–$C_{12}$), —OC(=O)N(R)$_2$ or —OC(=O)$OR_7$, and R is hydrogen, alkyl ($C_1$–$C_4$), or phenyl and each R is the same or different, and $R_7$ is alkyl($C_1$–$C_{12}$);

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, O(C=O)$R_{27}$ or O(C=O)$CH_2C(=O)OR_{26}$ $R_{10}$ is —C≡CH, —CH=$CH_2$, halogen, CN, $N_3$, $OR_{26}$, OC(=O)$R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, OC(=O)$R_{27}$, $NH_2$, $NHR_{26}$, NHC(=O)$R_{27}$, N($R_{26}$)$_2$, NC(=O)$R_{27}$, $N_3$, H, —OH, =O, —O—P(=O)(OH)$_2$, or —O—C(=O)—($CH_2$)$_t$COOH where t is an integer from 2 to 6;

$R_{14}$ is H or forms a double bond with $R_{12}$;

$R_{15}$ is H, =O or —OH;

$R_{23}$ is —OH, O—C(=O)—$R_{11}$, —OP(O)—(OH)$_2$, —O—C(=O)—($CH_2$)$_t$COOH or $R_{23}$ with $R_{10}$ forms a cyclic phosphate wherein t is an integer from 2 to 6; and $R_{11}$ is —Y—($CH_2$)$_n$—X—($CH_2$)$_m$—$SO_3H$, —Y'—($CH_2$)$_p$—X'—($CH_2$)$_q$—$NR_{16}R_{17}$ or —Z($CH_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S($O_2$)—; $R_{18}$ is hydrogen or alkyl ($C_1$–$C_4$); each of $R_{16}$ and $R_{17}$ is a lower alkyl group of from 1 to 4 carbon atoms optionally substituted with one hydroxyl;

n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) -$R_{19}$—$CH_2$COOH wherein $R_{19}$ is —S—, —S(O)—, —S(O)$_2$—, —$SO_2$N($R_{20}$)—, or N($R_{20}$)$SO_2$—; and $R_{20}$ is hydrogen or lower alkyl-($C_1$–$C_4$); with the proviso that the total number of carbon atoms in $R_{20}$ and ($CH_2$)$_r$ is not greater than 10; or (2) —CO—COOH; or (3) CON($R_{21}$)CH($R_{22}$)COOH wherein $R_{21}$ is H and $R_{22}$ is H, $CH_3$, —$CH_2$COOH, —$CH_2CH_2$COOH, —$CH_2$OH, —$CH_2$SH, —$CH_2CH_2SCH_3$, or —$CH_2$Ph—OH wherein Ph—OH is p-hydroxyphenyl;

or $R_{21}$ is $CH_3$ and $R_{22}$ is H;

or —N($R_{21}$)CH($R_{22}$)COOH is —NHCH$_2$CONHCH$_2$COOH; and pharmaceutically acceptable salts thereof;

with the proviso that if $R_{23}$ is a phosphate, it must form a cyclic phosphate, with $R_{10}$ when $R_{13}$ is =O, except for the compound wherein $R_1$ is β-$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is α-F, $R_9$ is β-$CH_3$, $R_{10}$ is α-OH, $R_{13}$ and $R_{15}$ are =O and $R_{23}$ is —OP(O)—(OH)$_2$, $R_{24}$ is C, $C_1$–$C_2$ double bond, O;

$R_{25}$ is C($R_{15}$)$CH_2$—$R_{23}$, OH, $OR_{26}$, OC(=O)$R_{27}$, $R_{26}$, COOH, C(=O)$OR_{26}$, $CHOHCH_2OH$, $CHOHCH_2OR_{26}$, $CHOHCH_2OC(=O)R_{27}$, $CH_2CH_2OH$, $CH_2CH_2OR_{26}$, $CH_2CH_2OC(=O)R_{27}$, $CH_2CN$, $CH_2N_3$, $CH_2NH_2$, $CH_2NHR_{26}$, $CH_2N(R_{26})_2$, $CH_2OH$, $CH_2OR_{26}$, $CH_2O(C=O)R_{27}$, $CH_2O(P=O)(OH)_2$, $CH_2O(P=O)$ ($OR_{26}$)$_2$, $CH_2SH$, $CH_2S$—$R_{26}$, $CH_2SC(=O)R_{27}$, $CH_2NC(O)R_{27}$, C(O)$CHR_{28}OH$, C(=O)$CHR_{28}OR_{26}$, C(=O)$CHR_{28}OC(=O)R_{27}$ or $R_{10}$ and $R_{25}$ taken together may be =C($R_{28}$)$_2$, that is, an optionally alkyl substituted methylene group;

wherein $R_{26}$ is $C_1$–$C_6$ (alkyl, branched alkyl, cycloalkyl, haloalkyl, aralkyl, aryl); $R_{27}$ is $R_{26}$ or $OR_{26}$; $R_{28}$ is H, C1–C6 (alkyl, branched alkyl, cycloalkyl);

excepted from the compounds of Structure [A] are the compounds wherein $R_{23}$ is OH, OC(=O)$R_{11}$, OP(O)(OH)$_2$, or OC(=O)($CH_2$)$_t$COOH;

also excepted from the compounds of Structure are the compound 3,11β,17α,21-tetrahydroxy-5-pregnane-20-one (the 3-α, 5-β; 3-α, 5-α; 3-β, 5-α; and 3-β, 5-β isomers of tetrahydrocortisol) wherein $R_{15}$ is =O, $R_{10}$ is α-OH, $R_1$ is β-$CH_3$, $R_3$ is β-OH, $R_2$ is H, $R_4$ is H, $R_{13}$ is α- or β-OH, $R_{14}$ is H, $R_{12}$ is α- or β-H, $R_5$ is H, $R_6$ is H, $R_9$ is H, $R_{24}$ is C, and $R_{23}$ is OH; and methyltestosterone, wherein $R_1$ is $\beta$-$CH_3$, $R_2$ is H, $R_3$ is H, R is H, $R_5$ is H, $R_6$ is H, $R_9$ is H, $R_{10}$ is $\alpha$-$CH_3$, $R_{12}$ and $R_{14}$ form a $C_4$–$C_5$ double bond, $R_{13}$ is =O, $R_{24}$ is C and $R_{25}$ is $\beta$-OH; dihydrotestosterone, wherein $R_1$ is $\beta$-$CH_3$, $R_2$, $R_3$, $R_4$, $R_5$, $R_6$, $R_9$, $R_{10}$, and $R_{14}$ are H, $R_{12}$ is $\alpha$-H, $R_{13}$ is =O, $R_{24}$ is C, and $R_{25}$ is $\beta$-OH; dromostanolone propionate, wherein $R_1$ is $\beta$-$CH_3$, $R_2$, $R_3$, $R_4$, $R_5$, $R_6$, $R_9$, $R_{10}$, and $R_{14}$ are H, $R_{12}$ is $\alpha$-H, $R_{13}$ is =O, $R_{24}$ is C and $R_{25}$ is $\beta$-OC(=O)$CH_2CH_3$; methandrostenelone, wherein R is $\beta$-$CH_3$, $R_2$, $R_3$, $R_4$, $R_5$, $R_6$, and $R_9$ are H, $R_{10}$ is $\alpha$-$CH_3$, $R_{12}$ and $R_{14}$ form a $C_4C_5$ double bond, $R_{13}$ is =O, $R_{24}$ is $C_1C_2$ double bond, and $R_{25}$ is $\beta$-OH; testosterone, wherein $R_1$ is $\beta$-$CH_3$, $R_2$, $R_3$, $R_4$, $R_5$, $R_6$, $R_9$, and $R_{10}$ are H, $R_{12}$ and $R_{14}$ form a $C_4C_5$ double bond, $R_{13}$ is =O, $R_{24}$ is C, and $R_{25}$ is $\beta$-OH; norethandrolone, wherein $R_1$ is $CH_3(C_{13})$ and $H(C_{10})$, $R_2$, $R_3$, $R_4$, $R_5$, $R_6$, and $R_9$ are H, $R_{10}$ is $\alpha$-$CH_2CH_3$, $R_{12}$ and $R_{14}$ form a $C_4$–$C_5$ double bond, $R_{13}$ is =O, $R_{24}$ is C, and $R_{25}$ is $\beta$-OH; bolasterone, wherein $R_1$ is $\beta$-$CH_3$, $R_2$, $R_3$, $R_4$, $R_5$, and $R_9$ are H, $R_6$ is $\alpha$-$CH_3$, $R_{10}$ is $\alpha$-$CH_3$, $R_{13}$ is =O, $R_{12}$ and $R_{14}$ form a $C_4C_5$ double bond, $C_{24}$ is C and $R_{25}$ is $\beta$-OH; and oxandrolone, wherein $R_1$ is $\beta$-$CH_3$, $R_2$, $R_3$, $R_5$, $R_6$, $R_9$, and $R_{14}$ are H, $R_{10}$ is $\alpha CH_3$, $R_{12}$ is $\alpha$-H, $R_{13}$ is =O, $R_{24}$ is O, and $R_{25}$ is $\beta$-OH; also excepted from the compounds of Structure A are 4,9(1 1)-Pregnadien-17$\alpha$,21-diol-3,20-dione-21 acetate, 4,9(11)-Pregnadiene-17$\alpha$,21-diol-3,20-dione, 11-epicortisol, 17$\alpha$ hydroxyprogesterone, and tetrahydrocortexolone.

2. The method of claim 1 wherein the neovascularization being prevented and treated is selected from the group consisting of head trauma, spinal trauma, septic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, neovascular glaucoma, nonunion fractures, Osler-Weber Syndrome, psoriasis, pyogenic granuloma, retrolental fibroplasia, scleroderma, solid tumors, trachoma, vascular adhesions, pterigium and solid tumor growth.

3. A method for preventing and treating ocular neovascularization, which comprises: administering a therapeutically effective amount of a composition comprising a compound of the formula:

Structure

Structure wherein $R_1$ is H, $\beta$-$CH_3$ or $\beta$-$C_2H_5$;

$R_2$ is F, $C_9$–$C_{11}$ double bond, $C_9$–$C_{11}$ epoxy, H or Cl;

$R_3$ is H, $OR_{26}$, OC(=O)$R_{27}$, halogen, $C_9$–$C_{11}$ double bond, $C_9$–$C_{11}$ epoxy, =O, —OH, —O— alkyl ($C_1$–$C_{12}$), —OC(=O)alkyl($C_1$–$C_{12}$), —OC(=O)N (R)$_2$ or —OC(=O)$OR_7$, and R is hydrogen, alkyl ($C_1$–$C_4$), or phenyl and each R is the same or different, and $R_7$ is alkyl($C_1$–$C_{12}$);

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, O(C=O)$R_{27}$ or O(C=O)$CH_2(C=O)OR_{26}$ $R_{10}$ is —C≡CH, —CH=$CH_2$, halogen, CN, $N_3$, $OR_{26}$, OC(=O)$R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, OC(=O)$R_{27}$, $N_2$, $NHR_{26}$, NHC(=O)$R_{27}$, N($R_{26}$)$_2$, NC(=O)$R_{27}$, $N_3$, H, —OH, =O, —O—P(=O)(OH)$_2$, or —O—C(=O)—($CH_2$)$_t$COOH where t is an integer from 2 to 6;

$R_{14}$ is H or forms a double bond with $R_{12}$;

$R_{15}$ is H, =O or —OH;

$R_{23}$ is —OH, O—C(=O)—$R_{11}$, —OP(O)—(OH)$_2$, —O—C(=O)—($CH_2$)$_t$COOH or $R_{23}$ with $R_{10}$ forms a cyclic phosphate wherein t is an integer from 2 to 6; and $R_{11}$ is —Y—($C_2$)$_n$—X—($C_2$)$_m$—$SO_3$H, —Y'—($C_2$)$_p$—X'—($C_2$)$_q$—$NR_{16}R_{17}$ or —Z($CH_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S($O_2$)—;

$R_{18}$ is hydrogen or alkyl ($C_1$–$C_4$); each of $R_{16}$ and $R_{17}$ is a lower alkyl group of from 1 to 4 carbon atoms optionally substituted with one hydroxyl;

n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2COOH$ wherein $R_{19}$ is —S—, —S(O)—, —S(O)$_2$—, —$SO_2N(R_{20})$—, or $N(R_{20})SO_2$—; and $R_{20}$ is hydrogen or lower alkyl-($C_1$–$C_4$); with the proviso that the total number of carbon atoms in $R_{20}$ and ($CH_2$)$_r$ is not greater than 10; or (2) —CO—COOH; or (3) $CON(R_{21})CH(R_{22})COOH$ wherein $R_2$, is H and $R_{22}$ is H, $CH_3$, $—CH_2COOH$, $—CH_2CH_2COOH$, $—CH_2OH$, $—CH_2SH$, $—CH_2CH_2SCH_3$, or $—CH_2Ph—OH$ wherein Ph—OH is p-hydroxyphenyl;

or $R_{21}$ is $CH_3$ and $R_{22}$ is H;

or $—N(R_{21})CH(R_{22})COOH$ is $—NHCH_2CONHCH_2COOH$; and pharmaceutically acceptable salts thereof;

with the proviso that if $R_{23}$ is a phosphate, it must form a cyclic phosphate, with $R_{10}$ when $R_{,3}$ is =O, except for the compound wherein $R_1$ is β-$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is α-F, R, is β-$CH_3$, $R_{10}$ is α-OH, $R_{13}$ and $R_{15}$ are =O and $R_{23}$ is $—OP(O)—(OH)_2$, $R_{24}$ is C, $C_1$–$C_2$ double bond, O;

$R_{25}$ is $C(R_{15})CH_2—R_{23}$, OH, $OR_{26}$, $OC(=O)R_{27}$, $R_{26}$, COOH, $C(=O)OR_{26}$, $CHOHCH_2OH$, $CHOHCH_2OR_{26}$, $CHOHCH_2OC(=O)R_{27}$, $CH_2CH_2OH$, $CH_2CH_2OR_{26}$, $CH_2CH_2OC(=O)R_{27}$, $CH_2CN$, $CH_2N_3$, $CH_2NH_2$, $CH_2NHR_{26}$, $CH_2N(R_{26})_2$, $CH_2OH$, $CH_2OR_{26}$, $CH_2O(C=O)R_{27}$, $CH_2O(P=O)(OH)_2$, $CH_2O(P=O)(OR_{26})_2$, $CH_2SH$, $CH_2S—R_{26}$, $CH_2SC(=O)R_{27}$, $CH_2NC(=O)R_{27}$, $C(=O)CHR_{28}OH$, $C(=O)CHR_{28}OR_{26}$, $(=O)CHR_{28}OC(=O)R_{27}$ or $R_{10}$ and $R_{25}$ taken together is $=C(R_{28})_2$, that is, an optionally alkyl substituted methylene group;

wherein $R_{26}$ is $C_1$–$C_6$ (alkyl, branched alkyl, cycloalkyl, haloalkyl, aralkyl, aryl); $R_{27}$ is $R_{26}$ or $OR_{26}$; $R_{28}$ is H, $C_1$–$C_6$ (alkyl, branched alkyl, cycloalkyl);

excepted from the compounds of Structure are the compounds wherein $R_{23}$ is OH, $OC(=O)R_{11}$, $OP(O)(OH)_2$, or $OC(=O)(CH_2)_tCOOH$;

also excepted from the compounds of Structure are the compound 3,11β,17α,21-tetrahydroxy-5-pregnane-20-one (the 3-α, 5-β; 3-α, 5-α; 3-β, 5-α; and 3-β, 5-β isomers of tetrahydrocortisol) wherein $R_{15}$ is =O, $R_{10}$ is α-OH, $R_1$ is β-$CH_3$, $R_3$ is β-OH, $R_2$ is H, $R_4$ is H, $R_{13}$ is α- or β-OH, $R_{14}$ is H, $R_{12}$ is α- or β-H, $R_5$ is H, $R_6$ is H, $R_9$ H, $R_{24}$ is C, and $R_{23}$ is OH; and methyltestosterone, wherein $R_1$ is β-$CH_3$, $R_2$ is H, $R_3$ is H, $R_4$ is H, $R_5$ is H, $R_6$ is H, $R_9$ is H, $R_{10}$ is α-$CH_3$, $R_{12}$ and $R_{14}$ form a $C_4$–$C_5$ double bond, $R_{13}$ is =O, $R_{24}$ is C and $R_{25}$ is β-OH; dihydrotestosterone, wherein $R_1$ is β-$CH_3$, $R_2$, $R_3$, $R_4$, $R_5$, $R_6$, $R_9$, $R_{10}$, and $R_{14}$ are H, $R_{12}$ is α-H, $R_{13}$ is =O, $R_{24}$ is C, and $R_{25}$ is —OH; dromostanolone propionate, wherein $R_1$ is β-$CH_3$, $R_2$, $R_3$, $R_4$, $R_5$, $R_6$, $R_9$, $R_{10}$, and $R_{14}$ are H, $R_{12}$ is α-H, $R_{13}$ is =O, $R_{24}$ is C and $R_{25}$ is β-$OC(=O)CH_2CH_3$; methandrostenelone, wherein $R_1$ is β-$CH_3$, $R_2$, $R_3$, $R_4$, $R_6$, and $R_9$ are H, $R_{10}$ is α-$CH_3$, $R_{12}$ and $R_{14}$ form a $C_4C_5$ double bond, $R_{13}$ is =O, $R_{24}$ is $C_1C_2$ double bond, and $R_{25}$ is β-OH; testosterone, wherein $R_1$ is β-$CH_3$, $R_2$, $R_3$, $R_4$, $R_5$, $R_6$, $R_9$, and $R_{10}$ are H, $R_{12}$ and $R_{14}$ form a $C_4C_5$ double bond, $R_{13}$ is =O, $R_{24}$ is C, and $R_{25}$ is β-OH; norethandrolone, wherein $R_1$ is $CH_3(C_{13})$ and $H(C_{10})$, $R_2$, $R_3$, $R_4$, $R_5$, $R_6$, and $R_9$ are H, $R_{10}$ is α-$CH_2CH_3$, $R_{12}$ and $R_{14}$ form a $C_4$–$C_5$ double bond, $R_{13}$ is =O, $R_{24}$ is C, and $R_{25}$ is β-OH; bolasterone, wherein $R_1$ is β-$CH_3$, $R_2$, $R_3$, $R_4$, $R_5$, and $R_9$ are H, $R_6$ is α-$CH_3$, $R_{10}$ is α-$CH_3$, $R_{13}$ is =O, $R_{12}$ and $R_{14}$ form a $C_4C_5$ double bond, $C_{24}$ is C and $R_{25}$ is β-OH; and oxandrolone, wherein $R_1$ is β-$CH_3$, $R_2$, $R_3$, $R_5$, $R_6$, $R_9$, and $R_{14}$ are H, $R_{10}$ is α$CH_3$, $R_{12}$ is α-H, $R_{13}$ is =O, $R_{24}$ is O, and $R_{25}$ is β-OH; also excepted from the compounds of Structure are 4,9(11)-Pregnadien-17α,21-diol-3,20-dione-21-acetate, 4,9(11)-Pregnadien-17α,21-diol-3,20-dione, 11-Epicortisol, 17α-Hydroxyprogesterone, and Tetrahydrocortexolone.

4. The method of claim 3 wherein the angiostatic steroid concentration is 0.01–10 wt. % of the composition.

5. The method of claim 3 wherein the angiostatic steroid concentration is 0.1 to 5.0 wt. % of the composition.

6. The method of claim 3 wherein the ocular neovascularization being prevented and treated is in the front of the eye.

7. The method of claim 3 wherein the ocular neovascularization being treated is in the cornea.

8. The method of claim 3 wherein the ocular neovascularization being prevented and treated is in the back of the eye.

9. A method for preventing and treating ocular neovascularization, which comprises: administering a therapeutically effective amount of a composition comprising a compound selected from the group consisting of: 21-nor-5β-pregnan-3α,17α,20-triol-3-acetate; 21-nor-5α-pregnan-3α,17α,20-triol-3-phosphate; 21-nor-5β-pregn-17(20)en-3α,16-diol; 21-nor-5β-pregnan-3α,17β,20-triol; 20-acetamide-21-nor-5β-pregnan-3α,17α-diol-3-acetate; 3β acetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-one-21-methyl ether; 20-azido-21-nor-5β-pregnan-3α,17α-diol; 20(carbethoxymethyl)thio-21-nor-5β-pregnan-3α,17α-diol; 20-(4-fluorophenyl)thio-21-nor-5β-pregnan-3α,17α-diol; 16α-(2-hydroxyethyl)-17β-methyl-5β-androstan-3α,17α-diol; 20-cyano-21-nor-5β-pregnan-3α,17α-diol; 17α-methyl-5β-androstan-3α,17β-diol; 21-nor-5β-pregn-17(20)en-3α-ol; 21-or-5β-pregn-17(20)en-3α-ol-3-acetate; 21-nor-5-pregn-17(20)-en-3α-ol-16-acetic acid 3-acetate; 3β-azido-5β-pregnan-11β,17α,21-triol-20-one-21-acetate; and 5β-pregnan-11β,17α,21-triol-20-one; 4-androsten-3-one-17β-carboxylic acid; 17α-ethynyl-5(10)-estren-17β-ol-3-one; 17α-ethynyl-1,3,5(10)-estratrien-3,17β-diol.

10. A method for preventing and treating neovascularization of the tissues in the front of the eye, which comprises: administering a pharmaceutically effective amount of a composition comprising a compound selected from the group consisting of: 21-nor-5β-pregnan-3α,17α,20-triol-3-acetate; 21-nor-5α-pregnan-3α,17β,20-triol-3-phosphate; 21-nor-5β-pregn-17(20)en-3α,16-diol; 21-nor-5β-pregnan-3α,17β,20-triol; 20-acetamide-21-nor-5β-pregnan-3α,17α-diol-3-acetate; 3β acetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-one-21-methyl ether; 20-azido-21-nor-5β-pregnan-3α,17α-diol; 20(carbethoxymethyl)thio-21-nor-5β-pregnan-3α,17α-diol; 20-(4-fluorophenyl)thio-21-nor-5β-pregnan-3α,17α-diol; 16α-(2-hydroxyethyl)-17β-methyl-5β-androstan-3α,17α-diol; 20-cyano-21-nor-5β-pregnan-3α,17α-diol; 17α-methyl-5-androstan-3α,17β-diol; 21-nor-5β-pregn-17(20)en-3α-ol; 21-nor-5β-pregn-17(20)en-3α-ol-3-acetate; 21-Nor-5β-pregn-17(20)-en-3α-ol-16-acetic acid 3-acetate; 3β-azido-5β-pregnan-11β,17α,21-triol-20-one-21-acetate; and 5β-pregnan-11β,17α,21-triol-20-one; 4-androsten-3-one-17β-carboxylic acid; 17α-ethynyl-5(10)-estren-17β-ol-3-one; 17α-ethynyl-1,3,5(10)-estratrien-3,17β-diol.

11. The method of claim 10 wherein the angiostatic steroid is administered at a concentration of about 0.01 to 10.0 weight percent of the composition.

12. A method for preventing and treating neovascularization of the tissues of the back of the eye, which comprises: administering a pharmaceutically effective amount of a composition comprising a compound selected from the group consisting of: 21-nor-5β-pregnan-3α,17α,20-triol-3-acetate; 21-nor-5α-pregnan-3α,17α,20-triol-3-phosphate; 21-nor-5β-pregn-17(20)en-3α,16-diol; 21-nor-5-pregnan-3α,17α,20-triol; 20-acetamide-21-nor-5β-pregnan-3α,17α-diol-3-acetate; 3β acetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-one-21-methyl ether; 20-azido-21-nor-5-pregnan-3α,17α-diol; 20(carbethoxymethyl)thio-21-nor-5β-pregnan-3α,17α-diol; 20-(4-fluorophenyl)thio-21-nor-5β-pregnan-3α,17α-diol; 16α-(2-hydroxyethyl)-17α-methyl-5β-androstan-3α,17α-diol; 20-cyano-21-nor-5-pregnan-3α,17α-diol; 17α-methyl-5β-androstan-3α,17β-diol; 21-nor-5β-pregn-17(20)en-3α-ol; 21-nor-5β-pregn-17(20)en-3α-ol-3-acetate; 21-nor-5β-pregn-17(20)-en-3α-ol-16-acetic acid 3-acetate; 3β-azido-5β-pregnan-11β,17α,21-triol-20-one-21-acetate; and 5β-pregnan-11β,17α,21-triol-20-one; 4-androsten-3-one-17β-carboxylic acid; 17α-ethynyl-5(10)-estren-17β-ol-3-one; 17α-ethynyl-1,3,5(10)-estratrien- 3,17β-diol.

13. The method of claim 12 wherein the angiostatic steroid is administered at a concentration of about 0.01 to 10.0 weight percent of the composition.

14. The method of claim 13 wherein the angiostatic steroid is administered at a concentration of about 0.01 to 5.0 weight percent of the composition.

\* \* \* \* \*